(12) United States Patent
Ballard et al.

(10) Patent No.: US 8,685,424 B2
(45) Date of Patent: Apr. 1, 2014

(54) ANTIMICROBIAL SUBSTRATE

(75) Inventors: Robert L. Ballard, Orangeburg, SC (US); Bruce L. Anneaux, Lexington, SC (US); Joshua L. Manasco, West Columbia, SC (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 0 days.

(21) Appl. No.: 13/272,412

(22) Filed: Oct. 13, 2011

(65) Prior Publication Data

US 2012/0114722 A1 May 10, 2012

Related U.S. Application Data

(60) Provisional application No. 61/393,128, filed on Oct. 14, 2010.

(51) Int. Cl.
| | |
|---|---|
| A01N 25/10 | (2006.01) |
| A01N 59/16 | (2006.01) |
| B29C 47/80 | (2006.01) |
| D01F 6/12 | (2006.01) |
| D06M 10/00 | (2006.01) |
| H05B 7/00 | (2006.01) |

(52) U.S. Cl.
USPC ........... 424/409; 424/617; 424/618; 264/127; 264/211.17; 264/465; 977/788; 977/810

(58) Field of Classification Search
None
See application file for complete search history.

(56) References Cited

U.S. PATENT DOCUMENTS

| | | | |
|---|---|---|---|
| 4,043,331 A | 8/1977 | Martin et al. | |
| 4,044,404 A | 8/1977 | Martin et al. | |
| 4,127,706 A | 11/1978 | Martin et al. | |
| 4,323,525 A | 4/1982 | Bornat | |
| 4,552,707 A | 11/1985 | How | |
| 4,612,337 A | 9/1986 | Fox, Jr. et al. | |
| 4,689,186 A | 8/1987 | Bornat | |
| 5,019,096 A | 5/1991 | Fox, Jr. et al. | |
| 5,344,297 A | 9/1994 | Hills | |
| 5,562,986 A | 10/1996 | Yamamoto et al. | |
| 5,665,428 A | 9/1997 | Cha et al. | |
| 5,700,572 A | 12/1997 | Klatt et al. | |
| 5,702,658 A | 12/1997 | Pellegrin et al. | |
| 6,235,388 B1 | 5/2001 | Yamamoto et al. | |
| 6,296,863 B1 | 10/2001 | Trogolo et al. | |
| 6,436,135 B1 | 8/2002 | Goldfarb | |
| 6,679,913 B2 | 1/2004 | Homsy | |
| 6,753,454 B1 | 6/2004 | Smith et al. | |
| 6,863,852 B1 | 3/2005 | Ballard et al. | |
| 7,115,220 B2 | 10/2006 | Dubson et al. | |
| 7,244,272 B2 | 7/2007 | Dubson et al. | |
| 7,316,754 B2 | 1/2008 | Ide et al. | |
| 7,413,575 B2 | 8/2008 | Phaneuf et al. | |
| 7,416,559 B2 | 8/2008 | Shalaby | |
| 7,485,141 B2 | 2/2009 | Majercak et al. | |
| 7,524,527 B2 | 4/2009 | Stenzel | |
| 7,582,240 B2 | 9/2009 | Marin et al. | |
| 7,799,261 B2 | 9/2010 | Orr et al. | |
| 7,857,608 B2 | 12/2010 | Fabbricante et al. | |
| 7,947,069 B2 | 5/2011 | Sanders | |
| 7,981,353 B2 | 7/2011 | Mitchell et al. | |
| 8,178,030 B2 | 5/2012 | Anneaux et al. | |
| 2003/0100944 A1 | 5/2003 | Laksin et al. | |
| 2003/0195611 A1 | 10/2003 | Greenhalgh et al. | |
| 2003/0211135 A1 | 11/2003 | Greenhalgh et al. | |
| 2004/0051201 A1 | 3/2004 | Greenhalgh et al. | |
| 2004/0076792 A1 | 4/2004 | Green et al. | |
| 2005/0187605 A1 | 8/2005 | Greenhalgh et al. | |
| 2005/0196603 A1 | 9/2005 | Carr et al. | |
| 2006/0009839 A1 | 1/2006 | Tan | |
| 2006/0153904 A1* | 7/2006 | Smith et al. | 424/448 |
| 2006/0200232 A1 | 9/2006 | Phaneuf et al. | |
| 2006/0264140 A1 | 11/2006 | Andrady et al. | |
| 2007/0003603 A1* | 1/2007 | Karandikar et al. | 424/443 |
| 2007/0031607 A1 | 2/2007 | Dubson et al. | |
| 2007/0087027 A1 | 4/2007 | Greenhalgh et al. | |
| 2007/0207335 A1* | 9/2007 | Karandikar et al. | 428/560 |
| 2007/0244569 A1 | 10/2007 | Weber et al. | |
| 2008/0021545 A1 | 1/2008 | Reneker et al. | |

(Continued)

FOREIGN PATENT DOCUMENTS

| | | | | |
|---|---|---|---|---|
| DE | 202005010978 U1 | 10/2005 | ................ | D01F 1/10 |
| EP | 0 950 731 A1 | 10/1999 | ................ | D01F 6/12 |

(Continued)

OTHER PUBLICATIONS

Bokgi Son, Bong-Yeol Yeom, Sang Hun Song, Chang-Soo Lee, and Taek Sung Hwang. Antibacterial Electrospun Chitosan/Poly(vinyl alcohol) Nanofibers Containing Silver Nitrate and Titanium Dioxide. Journal of Applied Polymer Science, vol. 111, 2892-2899 (2009). (Published online Dec. 5, 2008).*

International Search Report & Written Opinion for PCT Application No. PCT/US11/056073, filed Oct. 13, 2011.

"Silver ion release from antimicrobial polyamide/silver composites"—Radhesh Kumar, Helmut Munstedt—Available online Jul. 6, 2004—pp. 2081-2088.

Electrospun Nanoparticle—Nanofiber Composites via a One-Step Synthesis—Carl D. Saquing, Joshua L. Manasco & Saad A. Khan—2009—pp. 944-951.

(Continued)

Primary Examiner — Frederick Krass
Assistant Examiner — Michael P Cohen
(74) Attorney, Agent, or Firm — Womble Carlyle Sandridge & Rice LLP

(57) ABSTRACT

A method of preparing antimicrobial-containing polymeric products is provided, the method involving electrospinning a dispersion comprising a dispersible polymer, a fiberizing polymer, and one or more antimicrobial agents. The electrospun material is heated to remove solvent and the fiberizing polymer, giving a nonwoven polymeric material having antimicrobial agent incorporated therein. The material can be in the form of, for example, a non-woven sheet, tube, or covering.

21 Claims, 9 Drawing Sheets

(56) References Cited

U.S. PATENT DOCUMENTS

| | | |
|---|---|---|
| 2008/0029617 A1 | 2/2008 | Marshall et al. |
| 2008/0110342 A1* | 5/2008 | Ensor et al. ............... 96/54 |
| 2008/0199506 A1 | 8/2008 | Horres et al. |
| 2008/0208323 A1 | 8/2008 | El-Kurdi et al. |
| 2008/0217807 A1 | 9/2008 | Lee et al. |
| 2008/0242171 A1 | 10/2008 | Huang et al. |
| 2009/0012607 A1 | 1/2009 | Kim et al. |
| 2009/0018643 A1 | 1/2009 | Hashi et al. |
| 2009/0136651 A1 | 5/2009 | Larsen et al. |
| 2009/0160099 A1 | 6/2009 | Huang |
| 2009/0248131 A1 | 10/2009 | Greenan |
| 2009/0280325 A1 | 11/2009 | Lozano et al. |
| 2009/0324680 A1 | 12/2009 | Reneker |
| 2010/0093093 A1 | 4/2010 | Leong et al. |
| 2010/0151245 A1 | 6/2010 | Law et al. |
| 2010/0190254 A1 | 7/2010 | Chian et al. |
| 2010/0304205 A1 | 12/2010 | Jo et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2012/0114722 A1 | 5/2012 | Ballard et al. |

FOREIGN PATENT DOCUMENTS

| | | | |
|---|---|---|---|
| EP | 2363516 | 9/2011 | |
| JP | 2002-266219 | 9/2002 | |
| JP | 2007-100230 | 4/2007 | |
| KR | 10-2000-0069242 | 11/2000 | ............... D01F 6/12 |
| KR | 100803176 B1 | 2/2008 | ............... D01F 1/10 |
| KR | 100871440 B1 | 11/2008 | ............... D01D 5/30 |
| KR | 10-2009-0058155 | 6/2009 | ............ B65D 65/40 |
| WO | WO 98/26115 | 6/1998 | |
| WO | WO 2010/080126 | 7/2010 | |
| WO | WO 2010/083530 | 7/2010 | |
| WO | WO 2010/083530 A3 | 7/2010 | ............... D04H 3/16 |
| WO | WO 2010083530 A2 * | 7/2010 | |
| WO | WO2010132636 | 11/2010 | |
| WO | WO 2011/017695 A1 | 2/2011 | ............. B29C 47/00 |
| WO | WO 2011/017698 A1 | 2/2011 | ............... A61F 2/06 |

OTHER PUBLICATIONS

Electrospinning of Antibacterial Poly(vinylidence fluoride) Nanofibers Containing Silver Nanoparticles—Jiang Yuan et al.—XP007911074—Journal of Applied Polymer Science, Nol. 116, 668-672 (2010).
European Search Report dated Aug. 20, 2013, from co-pending European patent application No. 11833384.8.
International Search Report and Written Opinion dated May 23, 2012 for PCT/US2012/023006.
Preparation of polytetrafluoroethylene ultrafine fiber mats with electrospinning process; Sijun et al.; Materials Science Forum vols. 675-677 (2011); pp. 827-830.
U.S. Appl. No. 13/787,327, filed Mar. 6, 2013, Hall et al.
U.S. Appl. No. 13/826,618, filed Mar. 14, 2013, Hall et al.
U.S. Appl. No. 13/827,775, filed Mar. 14, 2013, Lampropoulos et al.
U.S. Appl. No. 13/829,452, filed Mar. 14, 2013, Hall et al.
Notification of Reason for Refusal dated Sep. 17, 2013, which issued for co-pending Japanese patent application No. 2012-555215.
Disclosure at Tradeshow on Jan. 18-22, 2009 and Jan. 17-21, 2010.

* cited by examiner

ANTIMICROBIAL SUBSTRATE

CROSS-REFERENCE TO RELATED APPLICATION

The present application is based on and claims priority to U.S. Provisional Application 61/393,128, having a filing date of Oct. 14, 2010, the content of which is incorporated by reference herein in their entirety.

FIELD OF THE INVENTION

The present application is directed to the incorporation of antimicrobial agents into polymeric substrates and to materials produced thereby.

BACKGROUND OF THE INVENTION

The incorporation of antimicrobial agents into various types of materials is beneficial as they may endow the material with the ability to prevent and/or inhibit the growth of microorganisms. Various antimicrobial agents are known. For example, silver is a broad spectrum antimicrobial that is thought to act via irreversible binding of silver ions to nucleophilic groups in the cells of various microbes (i.e., bacteria, viruses, yeast, and fungi). This binding disrupts the reproduction of the cells, resulting in the death of the microbe. Silver (e.g., particular silver and silver coatings) and various silver compounds (e.g., ionic silver compounds) have therefore been incorporated into a variety of wound care products. Silver metal can be used where it can be converted to ionic form. For example, silver in contact with aqueous solutions forms silver oxide, which is slightly soluble in water and can form silver ions.

In addition to silver and silver compounds, inorganic nanoparticles have also elicited significant interest as microbial agents. Nano-structured materials have the potential to achieve specific processes and selectivity, especially in biological and pharmaceutical applications. Certain inorganic nanoparticles have been shown to exhibit novel and improved physical, chemical, and biological properties and functionality due to their nano-scale size. For example, various metal oxide nanoparticles have been shown to have good antimicrobial activity. Certain inorganic particles that have been reported to exhibit antimicrobial properties include nano-silver, various oxides and sulfides of nanomaterials (including titanium dioxide, selenium sulfide, cadmium oxide, and zinc oxide). The antimicrobial mode of action of such nanoparticles may be the targeting of the cellular fabric by hydroxyl radicals, thus increasing permeability, disrupting metabolism, waste excretion, and fabric stability. In some cases, metal oxide nanoparticles may be preferable to nano-silver because of cost considerations. Further, cadmium oxide and titanium dioxide are both non-toxic and chemically stable under exposure to both high temperatures and capable of photo catalytic oxidation.

Poly(tetrafluoroethylene), PTFE, is a thermoplastic that offers exceptional resistance to high temperatures and corrosive environments. Because it is inert and nontoxic, PTFE is often used in medical implants. Although it is useful for numerous applications, PTFE is difficult to process by conventional molten polymer techniques. One method by which PTFE can be processed is by extruding the material as a paste and then drawing it into various forms to produce fibers, ribbons, fabrics, or tubes. PTFE made in this fashion is referred to as "expanded PTFE" or "ePTFE." One further method for processing of PTFE is to combine PTFE dispersions with fiber forming polymers. The mixture can then be electrospun to produce nonwoven fabrics, coverings, bats, or composites based on nanofibers. These forms of PTFE are commonly sintered, at least in part, at high temperatures to develop desirable mechanical properties. For both ePTFE and electrospun PTFE, a porous structure is created with high surface area.

Electrostatic spinning is a known process, as illustrated, for example, in U.S. Pat. Nos. 2,158,416 to Formhals; 4,043,331 to Martin et al.; 4,044,404 to Martin et al.; 4,143,196 to Simm et al.; 4,287,139 to Guignard; 4,323,525 to Bornat; 4,432,916 to Logan; 4,689,186 to Bornat; and 6,641,773 to Kleinmeyer et al., and U.S. Patent App. Publ. No. 2010/0193999 to Anneaux et al., each of which is incorporated herein by reference in their entirety.

Due to the wide application of PTFE in medical and other applications, it would be beneficial to incorporate antimicrobial agents within PTFE to endow the material with antimicrobial properties. Both organic and inorganic antimicrobial agents have been previously incorporated into PTFE articles by soaking or coating the exterior of the article with ionic silver or silver metal. However, such coatings are difficult to apply and have a relatively short product life. Thus, there is a need for a means by which antimicrobial agents can be incorporated effectively and easily into PTFE.

SUMMARY OF THE INVENTION

The present invention relates to a method for the incorporation of one or more antimicrobial agents into a polymer capable of being provided in the form of a dispersion (e.g., PTFE) and to antimicrobial-containing polymeric products produced thereby. In specific embodiments, the method comprises incorporating antimicrobial agents into a material during processing (e.g., electrospinning) such that the antimicrobial agents are a part of the article being produced.

In certain aspects, the present invention provides a method for preparing a nonwoven material having one or more antimicrobial agents incorporated therein. For example, the method may comprise electrostatically spinning (i.e., electrospinning or "espinning") dispersions comprising antimicrobial agent using an orifice-based spinning apparatus or an open bath, free surface-based spinning apparatus and subsequently heating the resulting material. Exemplary apparatus for such techniques include, but are not limited to, wires, cylinders, spikes, sharp edges, or similar geometry spinning electrodes.

In certain aspects, the invention provides a method of making a nonwoven mat comprising one or more antimicrobial agents, comprising: providing a dispersion comprising: a fluorinated polymer; a fiberizing polymer; one or more antimicrobial agents; and a solvent; electrospinning said dispersion to give a mat precursor; and heating said mat precursor at a temperature and for a time sufficient to remove said solvent and said fiberizing polymer, in order to form a nonwoven mat. In some embodiments, the electrospinning comprises: providing an apparatus comprising a charge source and a target a distance from said charge source; providing a voltage source to create a first charge at said charge source and an opposing charge at said target wherein said dispersion is electrostatically charged by contact with said charge source; and collecting said electrostatically charged dispersion on said target.

In some aspects, the invention provides a method of making a PTFE mat comprising one or more antimicrobial agents, comprising: providing a dispersion comprising: PTFE; a fiberizing polymer; one or more antimicrobial agents; and a solvent; providing an apparatus comprising a charge source and a target a distance from said charge source; providing a voltage source to create a first charge at said charge source and an opposing charge or ground at said target wherein said dispersion is electrostatically charged by contact with said charge source; collecting said electrostatically charged dispersion on said target to form a mat precursor; and heating said mat precursor to remove said solvent and said fiberizing polymer, thereby forming said PTFE mat.

In certain embodiments, the one or more antimicrobial agents are selected from the group consisting of silver, silver compounds, metal oxides, metal sulfides, and mixtures thereof. For example, the one or more antimicrobial agents may comprise silver nanoparticles, titanium dioxide, selenium sulfide, cadmium oxide, and/or zinc oxide. The content of the one or more antimicrobial agents can vary; in some embodiments, the mat comprises the one or more antimicrobial agents in an amount of between about 10 ppm and about 10,000 ppm (e.g., between about 1,000 ppm and about 5,000 ppm).

In some embodiments, the fluorinated polymer is provided in the form of a resin (e.g., a dispersion in water) comprising about 50% to about 80% polymer solids by weight. The fluorinated polymer particle size can vary. In some embodiments, the fluorinated polymer has an average particle size of between about 0.1 μm and about 0.3 μm. The fluorinated polymer can, in certain embodiments, be selected from the group consisting of fluorinated ethylene propylene (FEP), polyvinylidene fluoride (PVDF), perfluoroalkoxy (PFA), a copolymer of tetrafluoroethylene, hexafluoropropylene and vinylidene fluoride (THV), poly(ethylene-co-tetrafluoroethylene) (ETFE), ethylene chlorotrifluoroethylene (ECTFE), PCTFE (polychlorotrifluoroethylene), and copolymers, blends, and derivatives thereof. In certain embodiments, the fluorinated polymer comprises polytetrafluoroethylene. The solvent can vary, but in certain embodiments, the solvent is water. The weight ratio of fiberizing polymer to fluorinated polymer can vary; for example, in some embodiments, the amount of fiberizing polymer is provided in an amount of between about 3.0 and about 5.5 percent by weight of the amount of fluorinated polymer. In certain embodiments, the fiberizing polymer has a solubility in the solvent of greater than about 0.5 weight percent at room temperature. One exemplary fiberizing polymer according to the invention is polyethylene oxide. The molecular weight of the fiberizing polymer can vary. For example, in certain embodiments, the fiberizing polymer (e.g., polyethylene oxide) has a number average molecular weight of from about 50,000 amu to about 4,000,000 amu.

The dispersion may be prepared such that it has a specific viscosity. For example, in some embodiments, the dispersion has a viscosity of greater than 50,000 cP (including, but not limited to, within the range of about 70,000 cP to about 150,000 cP). The voltage applied can vary and in certain embodiments, the voltage is about 2,000 to about 100,000 volts. In certain embodiments, the heating is conducted between about 350° C. and about 485° C.

In another aspect of the invention is provided a method of making a nonwoven fluorinated polymer mat comprising one or more antimicrobial agents. For example, in certain embodiments, the invention provides a method of making a nonwoven polytetrafluoroethylene mat comprising one or more antimicrobial agents, comprising: providing a dispersion comprising: polytetrafluoroethylene; polyethylene oxide; one or more antimicrobial agents selected from the group consisting of silver, silver compounds, metal oxides, metal sulfides, and mixtures thereof; and a solvent; electrospinning said dispersion to give a PTFE mat precursor; and heating said PTFE mat precursor at a temperature and for a time sufficient to remove said solvent and polyethylene oxide, in order to form a nonwoven PTFE mat.

In a further aspect of the invention is provided a material comprising a non-woven PTFE with embedded antimicrobial agents. In certain embodiments, the non-woven PTFE material is in the form of a sheet, tube, or covering. Such nonwoven PTFE materials have a wide range of possible applications. In some embodiments, filtration devices (e.g., for medical applications or military applications), personal protective equipment (e.g., surgical masks, antimicrobial wipes, garments and respiration devices), wound dressing, and/or implantable medical articles (e.g., tissue scaffolding, stents, grafts, and occlusion devices) comprising non-woven PTFE are provided.

BRIEF DESCRIPTION OF THE DRAWINGS

A full and enabling disclosure, including the best mode thereof, directed to one of ordinary skill in the art, is set forth more particularly in the remainder of the specification, which makes reference to the included figures.

DETAILED DESCRIPTION

Figure 1:
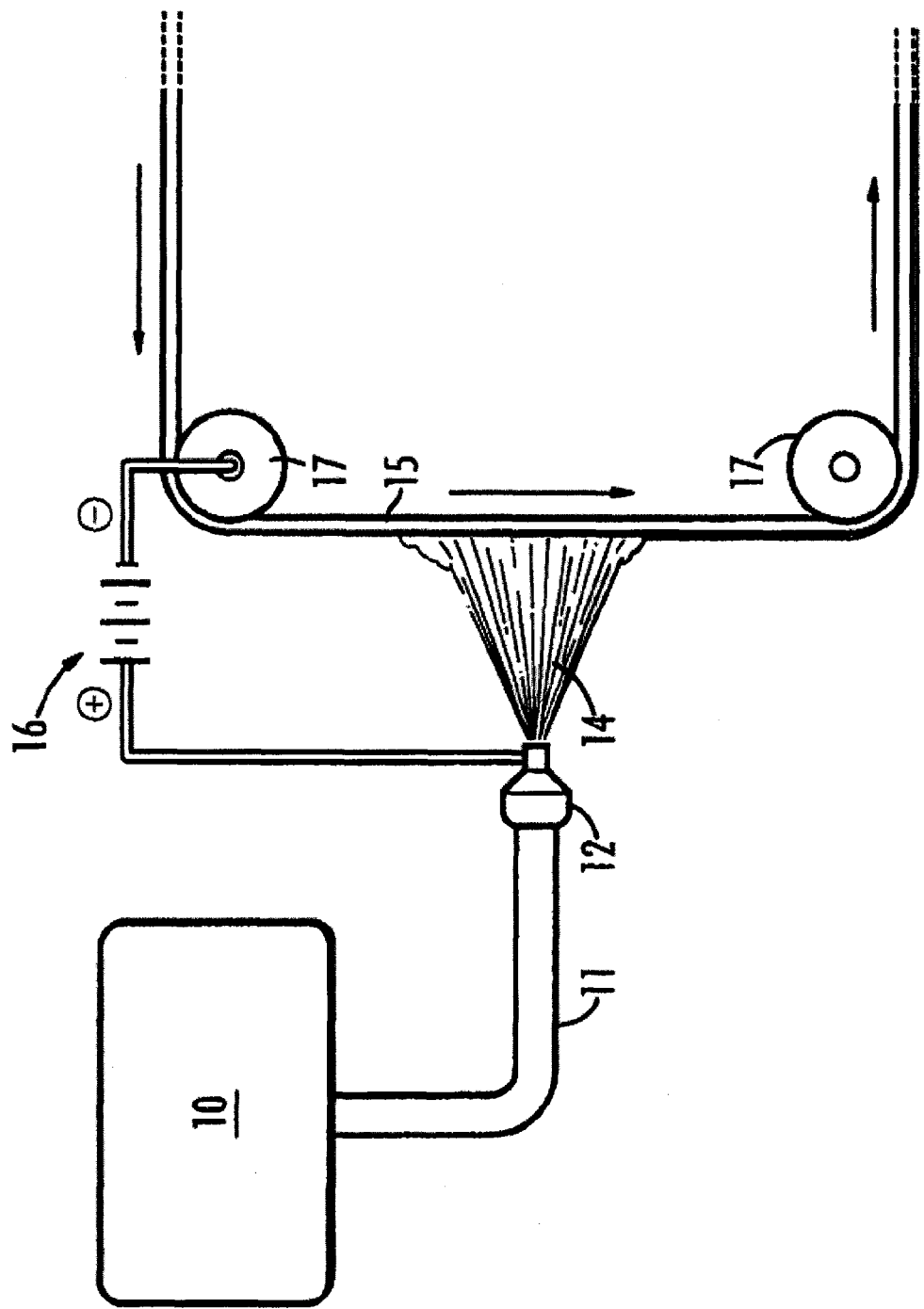
FIG. 1 is a schematic of an orifice (needle)-based electrospinning apparatus that may be used according to the present invention.

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention provides for the inclusion of one or more antimicrobial agents into a polymeric material. Generally, one or more antimicrobial agents and a polymeric material are combined and the resulting mixture is then processed by electrospinning or similar technique (i.e. centrifugal spinning, solution blowing, templating, etc.) to create a non-woven material. Preferably, the non-woven material is an electrospun (also referred to herein as "espun") polymeric material (e.g., including, but not limited to, PTFE). In certain aspects of the invention, a method for the preparation of electrospun PTFE comprising one or more antimicrobial agents is provided. In preferred embodiments, the one or more antimicrobial agents are incorporated into PTFE during processing, such that the antimicrobial agents are a part of the article that is produced. The method generally comprises electrospinning a dispersion comprising PTFE and one or more antimicrobial agents. Information related to processing and electrostatic spinning of PTFE from aqueous and other dispersions is provided, for example, in U.S. Pat. Nos. 4,323, 525 to Bornat and 4,044,404 to Martin et al., which are incorporated herein by reference in their entirety. In certain embodiments, the electrospinning process used according to the present invention is based at least in part, on the process described in U.S. Patent App. Publ. No. 2010/0193999 to Anneaux et al., which is incorporated herein by reference in their entirety.

Although the present description focuses on PTFE, it is noted that the methods and materials described herein may be applied to other polymer types. For example, in certain embodiments, any polymer that is capable of being provided in dispersion form can be used in place of PTFE in the methods detailed herein. For example, in some embodiments, polyether ether ketone (PEEK) is used. In some specific embodiments, the polymers comprise fluorinated polymers. For example, exemplary polymers that can be electrospun with antimicrobial agents according to the present invention include, but are not limited to, fluorinated ethylene propylene (FEP), polyvinylidene fluoride (PVDF), perfluoroalkoxy (PFA), a copolymer of tetrafluoroethylene, hexafluoropropylene and vinylidene fluoride (THV), poly(ethylene-co-tetrafluoroethylene) (ETFE), ethylene chlorotrifluoroethylene (ECTFE), PCTFE (polychlorotrifluoroethylene), and copolymers, blends, and derivatives thereof. It is understood that minor modifications of the parameters of the method described herein may be required to produce the desired material. One of skill in the art would be readily able to adjust such parameters as dispersion concentration, fiberizing polymer type, electrospinning time, heating time and heating temperature, among other parameters, to produce nonwoven antimicrobial-containing polymer materials analogous to the PTFE materials described herein.

The PTFE is typically provided as a dispersion (referred to herein as a "PTFE resin") and is typically an intimately mixed dispersion. The solids content of the PTFE resin is preferably between about 50% to about 80% by weight, and more preferably between about 55 and about 65% by weight. Certain PTFE resins useful according to the present invention are commercially available or can be prepared by combining PTFE with one or more solvents so as to produce a dispersion. One exemplary commercially available PTFE dispersion is Daikin D 210 PTFE, which comprises about 59-61 wt % PTFE solids (measured according to ASTM D 4441), 6.0-7.2% wt % surfactant, a pH at 25° C. of 8.5 to 10.5, a specific gravity of 1.50 to 1.53 and a Brookfield viscosity maximum of 35 cP. The properties of the PTFE (e.g., molecular weight, polydispersity index, particle size, particle size distribution) can vary. In some embodiments, the average particle size of the PTFE can be between about 0.05 μm and about 1 μm (for example, between about 0.1 μm and about 0.3 μm). In some embodiments, the average particle size is less than about 0.5 μm, less than about 0.4 μm, or less than about 0.3 μm. For example, the average particle size in certain embodiments may be about 0.14 μm, about 0.16 about 0.22 μm, or about 0.25 μm. In certain embodiments, the PTFE has a narrow particle size distribution. The solvent can be any solvent suitable for creating a dispersion, including, but not limited to, an aqueous solution or an alcohol solution (e.g., methanol, ethanol, or isopropanol).

The dispersion generally further comprises one or more fiberizing polymers. A fiberizing polymer is any polymer sufficient to facilitate the formation of a nonwoven web and which can preferably be removed following the electrospinning process to give a PTFE-based material. The fiberizing polymer is typically selected such that it has a high solubility in the solvent of the dispersion. For example, where the solvent is water, any water-soluble polymer can be used as the fiberizing polymer. Alternatively, where the solvent is alcohol, any alcohol-soluble polymer can be used. In certain embodiments for example, the fiberizing polymer can be selected from the group consisting of: polysaccharides (e.g., starch, chitosan, N-[(3'-hydroxy-2',3'-dicarboxy)ethyl]chitosan, dextran, and cellulosic polymers including cellulose ether, isopropyl cellulose, hydroxyethyl, hydroxylpropyl cellulose, cellulose acetate, cellulose nitrate, cellulose ethyl ether, cellulose ethyl hydroxyethyl ether, and cellulose methyl hydroxyethyl ether); gums (e.g., guar gum compounds, konjac glocomannan, pullulan, xanthan gum, i-carrageenan, alginates, alginic ammonium salts); polyacrylates (e.g., polyacrylic acid, poly(methacrylic acid), poly(2-hydroxyethyl acrylate), poly(2-(dimethylamino)ethyl methacrylate-co-acrylamide), poly(1-glycerol methacrylate), poly (2-hydroxyethyl methacrylate/methacrylic acid) 90:10, poly (2-hydroxypropyl methacrylate), poly(2-methacryloxyethyltrimethylammonium bromide), poly (ethyl acrylate/acrylic acid), poly(n-butyl acrylate/2-methacryloxyethyltrimethylammonium bromide), poly(3-chloro-2-hydroxypropyl-2-methacryloxyethyldimethylammonium chloride, dimethyl sulfatequaternary, and poly(ethylene/acrylic acid) 92:8); polyacrylamides and hydrolyzed polyacrylamides (e.g., poly (N-isopropylacrylamide), poly(2-acrylamido-2-methyl-1-propanesulfonic acid), 80:20, poly(acrylamide/acrylic acid), poly(acrylamide/2-methacryloxyethyltrimethylammonium bromide), poly(N-iso-propylacrylamide), poly(dimethyldodecyl(2-acrylamidoethyly)ammonium bromide)); polyamines (poly(vinyl amine), poly(4-amino-sulfo-aniline), polyethylene imine, poly(allylamine hydrochloride), polyaniline), poly(g-glutamic acid), poly(2-N-methylpyridinium-methylene iodine), poly(2-ethyl-2-oxazoline), poly[N-(p-sulfophenyl)amino-3-hydroxymethyl-1,4-phenyleneimino-1,4-phenylene)], poly(benzyltrimethylammonium chloride), and poly(1-lysine hydrobromide)); vinyl and vinylpyridine polymers (e.g., those that can be prepared from vinyl monomers, including, but not limited to, polyvinyl alcohol, poly (vinyl alcohol) 12% acetyl, polyvinylpyrrolidone, poly(vinyl sulfoxide), poly(N-vinyl pyrrolidone-co-vinyl acetate), poly (2-vinylpyridine), poly(4-vinylpyridine N-oxide), poly(4-vinylpyridine), poly(2-vinylpyridine N-oxide), poly(vinyl methyl ether), poly(vinylamine) hydrochloride, poly(vinylphosphonic acid), poly(vinylsulfonic acid) sodium salt, poly(2,4-dimethyl-6-triazinylethylene), poly(3-morpholinylethylene), poly(N-1,2,4-triazolyethylene), poly(methoxyethylene), poly(N-vinylpyrrolidone/2-dimethylaminoethyl methacrylate)); poly(N-propanoyliminoethylene), poly(N-methylpyridinium-2,5-diylethylene), poly(N-vinylpyrrolidone/vinyl acetate), poly(2-vinyl-1-methylpyridinium bromide), poly(diallyldimethylammonium chloride), poly (oxyethylene)sorbitan monolaurate, poly(4-N- butylpyridiniumethylene iodine), poly(styrenesulfonic acid), N-methyl-4(4'-formylstyryl)pyridinium, methosulfate acetal, poly(allylammonium chloride), poly(allyammonium phosphate), poly(itaconic acid), poly(diallyldimethylammonium chloride), poly(maleic acid), poly(butadiene/maleic acid)); polyethers (e.g., polyethylene oxide, poly(ethylene glycol) bis(2-aminoethyl), poly(ethylene glycol) monomethyl ether, poly(ethylene glycol)-bisphenol A diglycidyl ether adduct, and poly(ethylene oxide-b-propylene oxide)); and copolymers, derivatives, and blends thereof. One particularly preferred fiberizing polymer is polyethylene oxide.

The molecular weight of the fiberizing polymer can vary, but is typically greater than about 50,000 amu. Useful polymer molecular weights may vary according to the chemical makeup of the polymer. In one particular embodiment, the fiberizing polymer is polyethylene oxide with a molecular weight between about 50,000 to 4,000,000 amu (e.g., between about 200,000 amu and 600,000 amu). In certain embodiments, the polyethylene oxide fiberizing polymer has a number average molecular weight of about 200,000 amu, about 300,000 amu, about 400,000 amu, about 500,000 amu, or about 600,000 amu. The fiberizing polymer preferably has a high solubility in water (or other dispersion solvent), with a solubility of greater than about 0.5 wt % at room temperature being preferred. It is preferable that the fiberizing polymer has an ash content of less than about 5 wt %, when sintered at about 385° C., with even lower being more preferred.

The amount of fiberizing polymer present in the dispersion can vary; for example, in certain embodiments, the dispersion comprises about 1% to about 10% by weight of a fiberizing polymer. In certain embodiments, the weight ratio of fiberizing polymer to PTFE varies. For example, the amount of fiberizing polymer can be about 3.0% to about 5.5% that of the PTFE in the dispersion by weight. The amount of fiberizing polymer required according to the present invention may vary depending on the chemical makeup of the polymer.

The dispersion can be formed by any method known in the art. In some embodiments, the PTFE resin is mixed with the fiberizing polymer in aqueous solution to form a dispersion, which is then preferably allowed to homogenize. Although an aqueous mixture is generally used, it is noted that other solvents can be used without departing from the invention. In certain preferred embodiments, the solvent of the dispersion is the same solvent as that in the PTFE resin. The mixing time to form the dispersion can vary. Generally, the polymer dispersion is prepared so as to avoid high shear. In one preferred method, the polymer dispersion is allowed to form slowly, without agitation (for example, over the course of a few days, at which point the formation of a gel layer is apparent), followed by transfer to a jar roller that will turn jars of the polymer dispersion at a constant rate for several more days. A jar roller is a means to rotate jars to prepare and/or maintain uniformly mixed materials, where the jars are continually rotated at a speed of rotation that can typically be adjusted to ensure that the material is suitably mixed. Exemplary jar rollers are available, for example, from Diemat, Inc., the Mikrons® group, Paul N. Gardner Company, Detroit Process Machinery, and Paul O. Abbe. Any method can be used to produce the polymer dispersion that results in a material that is generally uniform by visual inspection and that has a suitable viscosity. It is noted that some inhomogeneity in the dispersion is acceptable; in certain embodiments, the polymer dispersion is filtered prior to spinning. The amount of solvent in the dispersion can be varied to obtain the desired consistency or viscosity.

One or more antimicrobial agents are added at any stage of the process described herein. The one or more antimicrobial agents are typically added to the mixture after the polymer dispersion has been formed. Generally, the one or more antimicrobial agents are added after formation of the polymer dispersion and the dispersion is mixed (e.g., by rotating in a jar roller as previously described) to distribute the one or more antimicrobial agents throughout the dispersion. The antimicrobial agents can be added in solid form or in the form of a solution or suspension. Although the polymer dispersion is generally formed before addition of the antimicrobial agents, it is noted that the antimicrobial agents may, in certain embodiments, be added at an earlier point in the process. For example, in some embodiments, it may be desirable to mix the antimicrobial agent with the fiberizing polymer or to mix the antimicrobial agent with the PTFE prior to combining the fiberizing polymer and the PTFE.

The types and amounts of antimicrobial agent added to the dispersion can vary. Any agents known or suspected to be capable of exhibiting antimicrobial capabilities (i.e., capable of slowing the growth of or killing microbes) can be used according to the invention. Antimicrobial agents include antifungals, antivirals, antibiotics, and antiparasitics. For example, certain antimicrobial agents include, but are not limited to, silver, silver ions, silver compounds, metal oxides (e.g., titanium dioxide, zinc oxide, and cadmium oxide), metal sulfides (e.g., selenium sulfide) and mixtures thereof.

The amount of the one or more antimicrobial agents is typically that amount sufficient to exhibit some degree of antimicrobial activity. The amount of antimicrobial agent needed to produce some antimicrobial activity typically varies depending on the specific antimicrobial agent selected. In some embodiments, the polymer dispersion comprises antimicrobial agent in an amount of from about 0.001% to about 20% by weight of the dispersion. For example, silver can be incorporated into or onto the PTFE at about 10-10,000 ppm, such as about 100-7,500 ppm, about 500-5,000 ppm, or about 1,000-5,000 ppm (e.g., about 2,500 ppm or about 5,000 ppm being adequate for demonstration of some of the advantages provided by the present invention).

In preferable embodiments, the viscosity of the dispersion is within a certain desirable range to allow for the formation of uniform and consistent fibers therefrom. For example, the present disclosure contemplates the use of dispersions with viscosities of greater than about 50,000 cP to provide for uniform and consistent fiber formation, as well as faster builds. For example, in some embodiments, the viscosity is between about 50,000 cP and about 300,000 cP (e.g., about 70,000 cP to about 150,000 cP). Viscosity can be measured, for example, with a Brookfield Viscometer. The desired viscosity of the dispersion may vary depending on the method of electrospinning to be conducted. For example, an orifice (needle)-based apparatus may require a somewhat higher viscosity than a free surfaced-based apparatus.

It is preferred to create a uniform solution that has little to no air trapped in the resulting highly viscous mixture. The dispersion can be treated in some way prior to being electrospun. For example, in certain preferred embodiments, the antimicrobial agent-containing dispersion is mixed to a relatively uniform consistency and is filtered to remove any clumps or gels.

The antimicrobial agent-containing dispersion is electrospun. For example, in certain embodiments, the dispersion is loaded into a controlled pumping device with a fixed conductive element which acts as the charge source. In one embodiment the conductive element is one with one or several orifices, where the dispersion is discharged through the orifice toward a target, where the orifice and target have opposing electrical charge (or wherein the target is at ground). For further details regarding apparatus that may be used according to the invention are provided, for example, in U.S. Patent Appl. Publ. No. 2010-0193999 to Anneaux et al., which is incorporated herein by reference in their entirety.

In certain embodiments, the electrospinning apparatus is as depicted in FIG. 1. In FIG. 1, a reservoir, 10, is loaded with a dispersion. A delivery system, 11 (e.g., a pumping device), delivers the dispersion from the reservoir to a charge source, 12, which may be an orifice. The ejection volume from the pumping device is set to a predetermined rate that is dependent on the form being made and the desired fiber diameters. Where an orifice-based system is used, the orifice size is preferably, but not limited to, about 0.01 mm to about 3.0 mm in diameter. A target, 15, is set some distance from the charge source, 12. A power source, 16, including (but not limited to) a DC power supply establishes an electrical charge differential between the charge source and the target such that the PTFE-containing dispersion, 14, is electrically charged opposite the target. The charge source is preferably connected to the positive side of a precision DC power supply. The negative side of the power supply is preferably connected to the collection surface or target. Although not preferred, the polarity can, in certain embodiments, be reversed. It is also possible for the target to be at ground. The PTFE-containing dispersion is electrostatically attracted to the target and deposited thereon. The target may be static or in motion (e.g., it may be a continuous or near continuous material that moves through the zone of impact, such as by movement on transport rollers, 17, or the like. Although not intended to be limiting, various electrospinning techniques are described, for example, in U.S. Pat. Nos. 6,743,273 to Chung et al. and 7,815,427 to Green et al., U.S. Patent Application Publication Nos. 2003/0017208 to Ignatious et al., 2008/0307766 to Petras et al., 2009/0127747 to Green et al., 2009/0199717 to Green et al., 2010/0018641 to Branham et al., and 2011/0111012 to Pepper et al., all of which are incorporated herein by reference in their entirety.

The collection surface can be, for example, a drum (i.e., a cylinder around which a material can be wrapped) or a sheet. A drum is typically rotated during deposition and the resulting three-dimensional material can be used in this "tube"-type form or can be cut to provide the electrospun material in sheet form. A sheet is a flat collection surface with discrete dimensions. In some further embodiments, the collection surface is any material that can be coated, i.e., covered. The shape, size, and geometry of the material to be covered can vary. For example, the collection surface can be a device, including but not limited to, implantable medical devices (e.g., tissue scaffolding, stents, grafts, and occlusion devices). In such embodiments, the electrospinning is conducted such that the device is covered with the PTFE-containing dispersion. In such embodiments, the device may be coated with another material prior to the electrospinning or the device can be directly covered, such that the electrospun material forms a covering layer on the device. The surface can be any metal, ceramic or polymeric material, with particularly preferred materials selected from stainless steel, cobalt chrome, nickel titanium (e.g., nitinol) and magnesium alloys. The voltage on the power supply is increased to the desired voltage to uniformly draw out the polymer/PTFE dispersion. The applied voltage can vary, but is typically from about 2,000 to about 100,000 volts. The charge induced by the connection of the power supply repels the charged polymer away from the charge source and attracts it to the collection surface. The collection target is preferably placed perpendicular to the pump and orifice system and is moved in at least one direction such that the entire surface is uniformly covered, with the fibers drawn towards the target. The collection surface can, in certain embodiments, be rotated to as to ensure coverage on all sides of the collection surface (e.g., where the collection surface comprises a drum or 3-dimensional device).

In an alternative embodiment, the PTFE dispersion is electrospun (e.g., into a fabric sheet) using an open bath electrospinning apparatus. For example, the apparatus can comprise a wire, cylinder, spike, sharp edge, or similar geometry spinning electrode. For the open bath unit, the ejection volume is dependent upon the viscosity of the dispersion, the conductivity of the dispersion, the surface tension of the dispersion, the distance from bath to target, and the voltage. These factors also affect the thickness of the fabric, and the desired fiber diameters so optimization of these parameters is required. The charge source is preferably connected to the positive side of a precision DC power supply. The negative side of the power supply is preferably connected to the collection surface. Alternatively, the collection surface can be at ground. The polarity can be reversed but this is not preferred. The applied voltage can vary, but is typically from about 40,000 to about 100,000 volts. The charge induced by the connection of the power supply repels the charged polymer away from the charge source and attracts it to the collection surface. In open bath electrospinning, the collection surface is typically a sheet. The sheet surface can be any metal or polymeric material with stainless steel being a particularly preferred material. The voltage on the power supply is increased to the desired voltage to uniformly draw out the polymer/PTFE solution and attract the solution to the target. The collection target is placed above the open bath and is moved in at least one direction such that the entire surface is preferably uniformly covered.

Once the collection surface has been adequately covered by any of the methods described herein, the material is preferably heated. The material can be heated in place (i.e., by placing the entire collection surface in an oven) or by removing the electrospun material from the collection surface prior to heating and placing the free electrospun material in an oven. The heating step can serve a number of purposes. It can serve to dry the material (e.g., by removing solvent from the electrospun product). The heating step can also serve to volatilize and remove the fiberizing polymer. The heating step additionally can result in sintering of the PTFE particles.

The time and temperature at which the material is heated can vary. For example, in typical embodiments, the temperature of the oven is between about 350° C. and about 485° C. The time for which the material is heated may depend, in part, on the temperature of the oven. The time can also depend on the thickness of the material, with thicker materials requiring more time to dry and/or sinter. In certain embodiments, the material is heated for an hour or less, although longer heating times can be used without departing from the invention.

The drying, volatilizing, and sintering can occur simultaneously or in a series of steps. While not intended to be limited by any theory, it is believed that some drying (i.e., removal of the solvent) may occur upon completion of electrospinning. It is further believed that some small degree of fiber rearrangement may occur at this point.

Then when the material is heated, preferably, the majority of the solvent and the fiberizing polymer (e.g., greater than about 80%, preferably greater than about 90% or 95%, and most preferably greater than about 98 or 99%) is removed from the PTFE material. It is well known to those skilled in the art that espun fabric undergoes shrinkage upon heating. While not limited to any theory the shrinkage is believed to occur in two steps: the initial drying and fiber rearrangement following the electrospinning process, and the removal of solvent and fiberizing polymer by heating.

As noted above, the heating can also result in sintering. Sintering refers to the fusion of individual PTFE particles to produce a nonwoven, PTFE-based material. The sintering of the material generally results in the formation of a stronger, more durable material. The level of sintering can vary. During heating, the material can be monitored to evaluate the sintering level by various methods (e.g., calorimetry). Heating generally causes the material to undergo physical changes that can be evaluated, e.g., visually. For example, if the material is visually sticky and still tacky, this generally suggests that the material should be heated longer. If there is discoloration (e.g., yellowing) of the material, it commonly indicates the presence (i.e., incomplete decomposition) of the fiberizing polymer and this also suggests that the material should be heated longer.

The product of the process described herein is a PTFE material comprising one or more antimicrobial agents. In certain embodiments, the material is white in color. Preferably, the antimicrobial agents are an integral part of the PTFE material. While not limited to any theory, the antimicrobial agent becomes integrated into the PTFE either as an included material or as a bound material on the surface. In certain embodiments, the antimicrobial agent is embedded within the nonwoven PTFE material. For example, antimicrobial agents may be embedded in a somewhat uniform fashion throughout the material. Typically, the antimicrobial agent is present at discrete locations within the PTFE material (i.e., in a non-continuous fashion). In other words, these materials are thus easily distinguishable from materials having a somewhat uniform layer of antimicrobial agent within the material. The espun material is preferably fibrous and can be described as a nonwoven material. In certain embodiments, the PTFE fibers are continuous. Particularly preferred espun fibers have a diameter of at least 0.1 μm. In a particularly preferred embodiment the product, after sintering, has fibers deposited in a density such there is a range of distances of about 0.1 μm to about 50 μm between points of contact. In certain embodiment, at least 90%, at least 95%, at least 98%, at least 99%, at least 99.9%, or 100% of the distances between points of contact fall within this range. However, it is noted that distances between points of contact can, in some embodiments, be significantly less and/or significantly more (i.e., less than about 0.1 μm and/or greater than about 50 μm between points of contact). The distances can be evaluated by estimating the distances between fibers as viewed through a scanning electron microscope. As noted, the material can comprise a range of different forms (e.g., non-woven sheet, tube, or covering) and can be useful in a wide variety of applications.

Electrospun PTFE containing antimicrobial agents represents a useful material for a wide variety of applications. Although not intended to be limiting, certain exemplary areas of potential use are highlighted herein. For example, antimicrobial agent-containing electrospun PTFE may advantageously be used in: filtration devices where microbial activity can hinder or prevent efficient separation; filtration devices where the bio burden and microbial fouling are of concern for the purity of the air such as in hospitals, clean rooms, military, nuclear, biological, and chemical warfare protection systems; personal protective equipment such as surgical masks, antimicrobial wipes, garments and respiration devices where it is essential for the protection of health and rescue workers against infection (especially as replacement of clean masks and gowns are not always possible in some emergency situations); exterior medical applications for wound care where the large surface areas of the electrospun PTFE provide great availability for antimicrobial activity; internal medical applications, where the antimicrobial action protects the article or implantation site from microbes introduced on the article or at the time of implantation (e.g., wound dressings, tissue scaffolding, stents, grafts, occlusion devices, and/or other implantable espun PTFE or composite devices containing espun PTFE).

Many other suitable materials can be espun in addition to or in combination with espun PTFE. In some embodiments, multiple polymers (which may or may not contain antimicrobial agents) can be espun from dispersions according to the methods provided herein, for example, to provide a multilayered composite material. Exemplary polymers that can be espun from dispersions are noted herein. Alternatively or in addition, the antimicrobial-containing dispersions described herein can be espun in addition to or in combination with traditional solution-espun materials. As known in the art, polymers that can be placed in solution have the potential to be espun. In accordance with the present disclosure, electrospinning of polymers including, but not limited to, nylons, polyurethanes (PU), polyesters, and the like, can be used in combination with the methods provided herein. Also, the electrospun materials can be combined with layers of various materials prepared by other methods known in the art to give composite materials. The present disclosure can be better understood with reference to the following examples.

EXAMPLES

In espun PTFE embodiments, the viscosity of the dispersion may be changed by the addition or removal of water from the dispersion without changing the fiberizing polymer (e.g., PEO) to PTFE ratio.

In all examples, Smartsilver® AS was first dispersed in 30 mL of 60° C. water while being agitated with a stir bar at 400 RPM. This was done by adding small quantities (0.25 g) of the Smartsilver® AS to 30 mL of water. After each addition, the material was allowed to disperse before making subsequent additions until 5 g total of the Smartsilver® AS was added. The solution was a dark, green slurry without any dark agglomerates visible to the naked eye. The solution was then diluted with 70 mL of cold water to make approximately 100 mL of total solution with a final concentration of 5% Smartsilver® AS (w/v). This solution was then added to the electrospinning PTFE dispersion made up of 1000 mL of Daikin D-210 PTFE dispersion with 40 grams of 300K molecular weight polyethylene oxide (PEO). The combined dispersion was allowed to turn for 48 hours to produce a well-mixed, viscous solution that was grey in color. At these conditions, the final product would contain approximately 2500 ppm of active silver. The resultant viscosity of this mixture was measured at 2.5 RPMs using a #25 spindle at 25° C. taken with a Brookfield LV Viscometer and determined to be approximately 74,000 cP.

Smartsilver® AS is an alcohol-soluble dispersible silver nanoparticle material provided by Nanohorizons, Inc. (State College, Pa.), containing only pure silver and a physiologically inert stabilizer (a polymer, whose structure is protected as a trade secret). The silver content is 51.9±2.6 w/w %. Smartsilver® WS is a water-soluble powder, comprising silver nanoparticles stabilized by a water-soluble polymer and is also provided by Nanohorizons, Inc.

All values referred to herein relate to the amount of "active silver," i.e., the amount of silver actually added, correcting for the percentage of silver contained in the added compound.

Example 1

Figure 2:
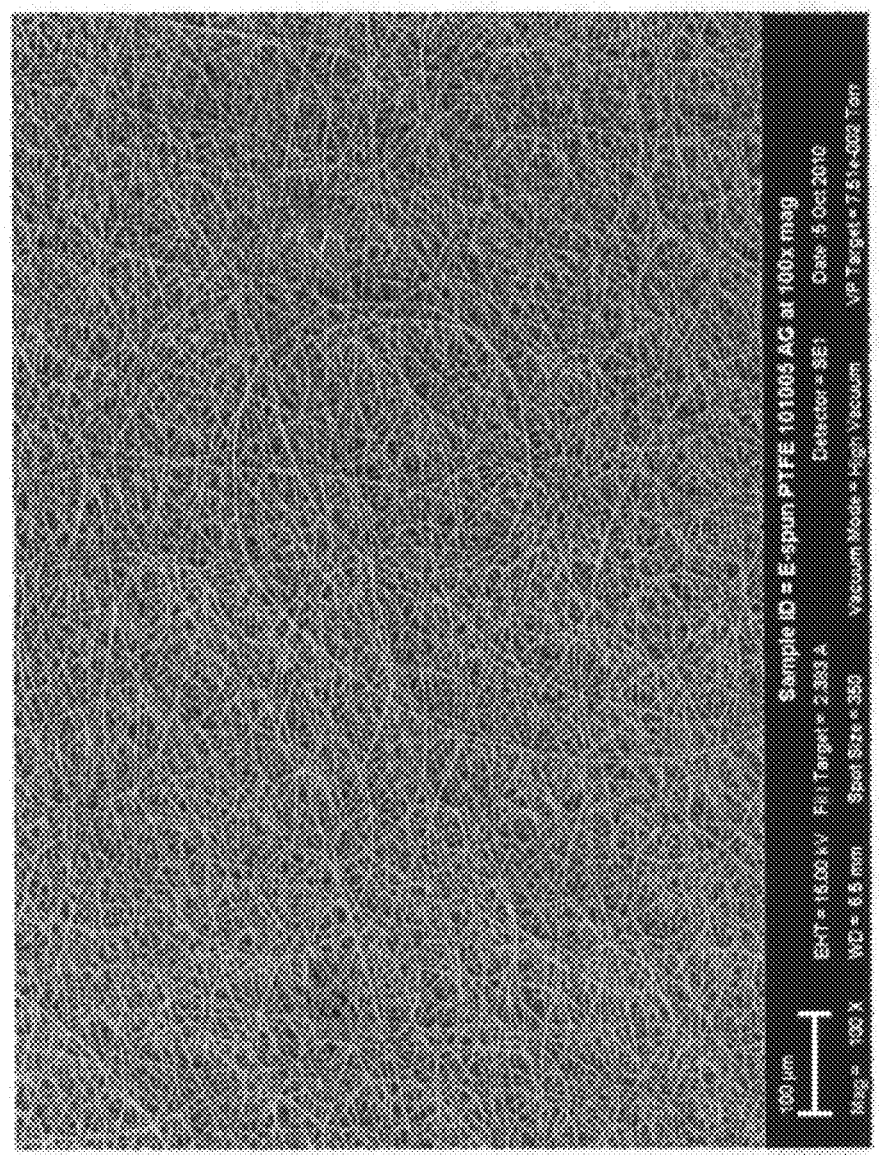
FIG. 2 is a low resolution SEM micrograph of PTFE fibers containing approximately 2500 ppm of active silver (Smartsilver® AS), electrospun from an orifice (needle)-based apparatus.
Figure 3:
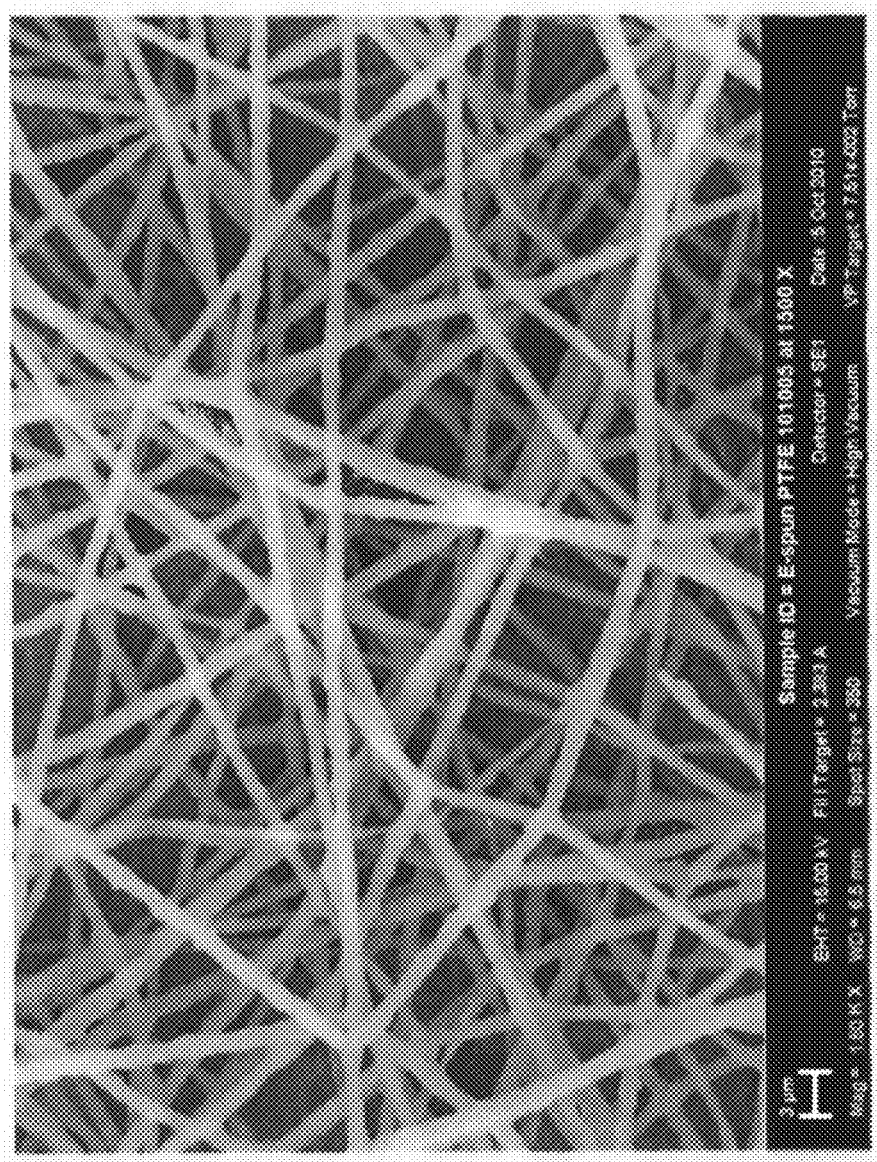
FIG. 3 is a high resolution SEM micrograph of PTFE fibers containing approximately 2500 ppm of active silver (Smartsilver® AS), electrospun from an orifice (needle)-based apparatus.

Fibers were made using an orifice (needle) based electrospinning apparatus. A stainless steel substrate was loaded on a mandrel which was mounted on a rotating arm and set to rotate at 20 RPM. The collection distance was set to approximately 7 inches. The voltage used to electrospin was between 10-20 kV. The syringe was placed into a KD Scientific Model 780200L syringe pump and set to a 0.5 ml/hour pumping rate. The needle tip was positioned at approximately 7" from the rotating drum assembly. The rotation of the drum assembly was approximately 60 rpm. A traverse was used to move the espinning needle along the length of the drum with a rate of travel of 3.0 mm/sec. This material was then sintered at 385° C. for approximately 5 minutes. Scanning Electron Microscope (SEM) images of the espun PTFE fabric containing 2500 ppm active silver, after sintering, are shown in FIGS. 2 and 3. Average fiber diameters were determined to be 1.15 μm+/−0.241 μm.

Example 2

Figure 4:
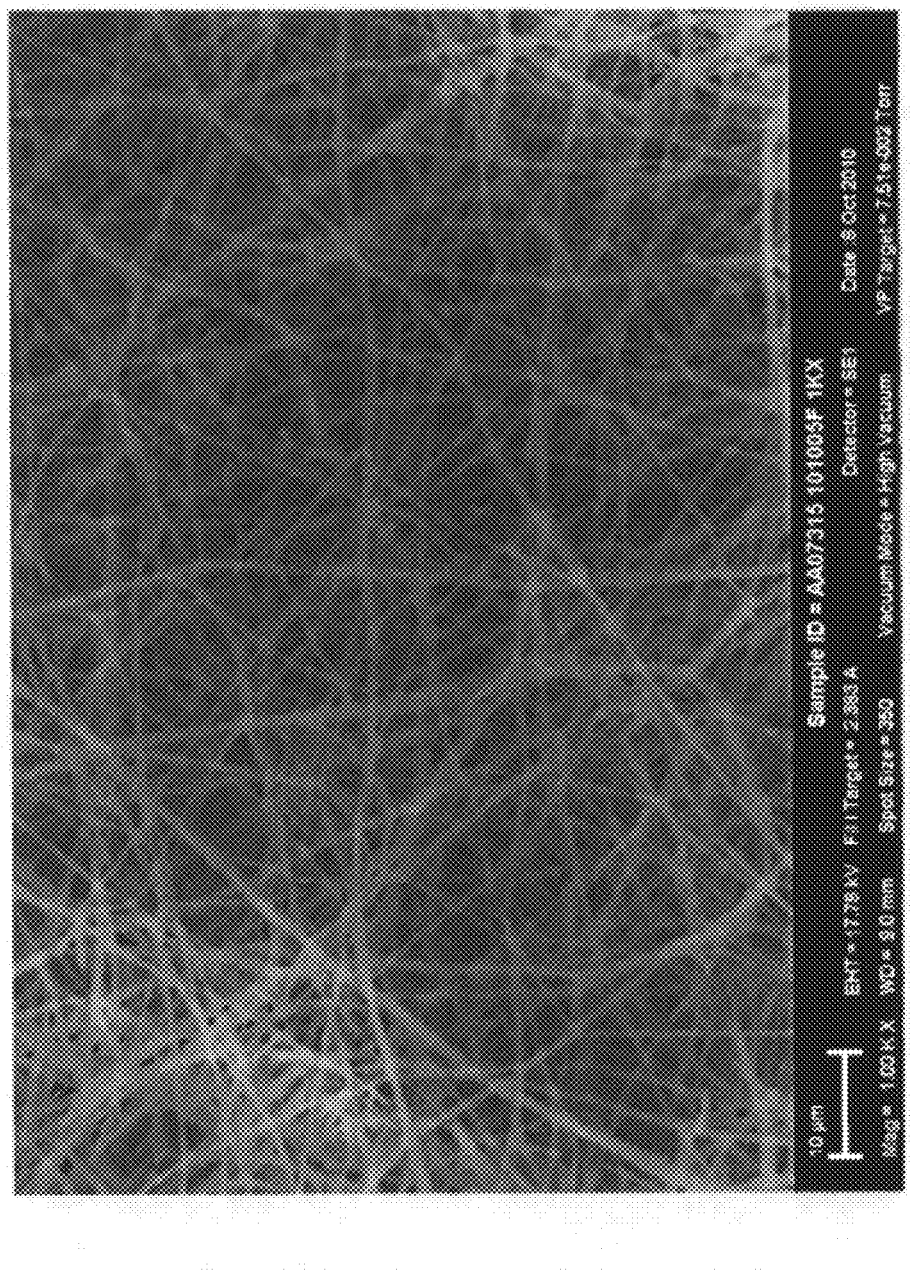
FIG. 4 is a SEM micrograph of PTFE fibers containing approximately 2500 ppm of active silver (Smartsilver® AS), electrospun from a free surface based apparatus.

PTFE electrospun fiber fabric containing 2500 ppm Smart-Silver® AS was also produced via free surface electrospinning similar to a wire or trough method. The solution was loaded into a bath where a cylindrical roller was used as the charging electrode and was coated with the aforementioned solution. A 0.002" thick stainless steel foil sheet (15.5"× 17.5") was mounted on a conductive fabric. The stainless foil was passed into the espinning chamber where the composite PTFE fibers were deposited. The collection distance used was approximately 230 cm and the voltage used was 60-70 kV. The sheets were collected using multiple passes of the substrate over the charging electrode at approximately 5 ft/min to produce a ~1.2 mil thick PTFE/SmartSilver® AS sheet. FIG. 4 shows the derived espun PTFE fabric. A summary of characterization techniques performed on the sample are provided below in Table 1.

TABLE 1

| | |
|---|---|
| Avg. Fiber Diameter and Std. Dev. (μm) | 0.675 ± 0.08 |
| Tensile Strength (Pa) | 189 ± 42.2 |
| Elongation (%) | 110 ± 8.2 |
| Gurley (sec/100 cc) | 2.7 ± 0.27 |
| Mean Pore Diameter (μm) | 2.28 ± 0.111 |
| Bubble Point Diameter (μm) | 692 ± 1190 |
| Basis Weight (g/m2) | 7.04 ± 0.335 |
| Thickness (μm) | 30.5 |
| Silver (% by weight) | 0.35 |

Example 3

Smartsilver® WS was loaded directly into the electrospinning dispersion containing 1000 mL of Daikin D-210 PTFE dispersion containing 40 g of PEO. The Smartsilver® WS was loaded such that the final fiber samples contains approximately 2500 ppm of active silver. The final solution was allowed to roll in a jar roller for over 48 hours to produce a viscous, grey-green solution. The resultant viscosity of this mixture was measured at 2.5 RPMs using a #25 spindle at 25° C. taken with a Brookfield LV Viscometer to be approximately 69,000 cP.

Figure 5:
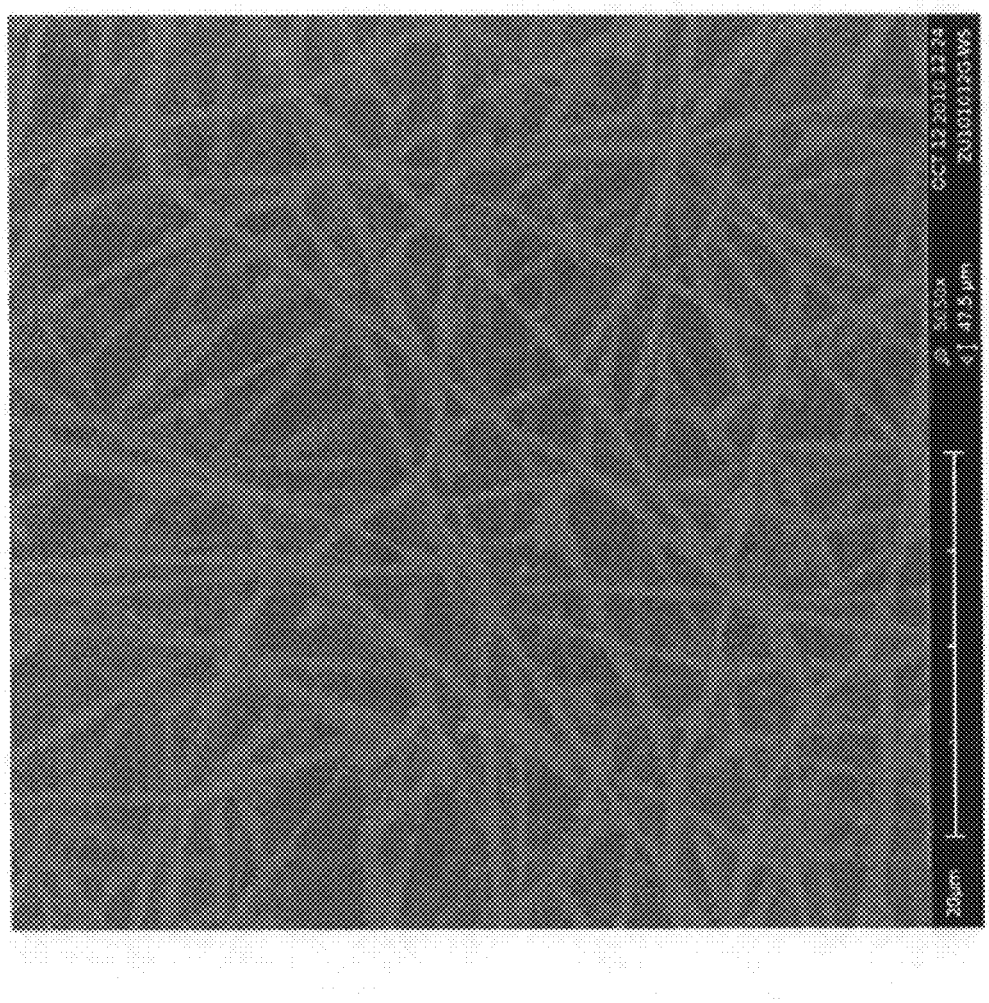
FIG. 5 is a SEM micrograph of PTFE fibers containing approximately 2500 ppm of active silver (Smartsilver® WS), electrospun using an orifice (needle)-based apparatus.

The PTFE dispersion containing the 2500 ppm Smartsilver® WS was used in an orifice based electrospinning system to produce an espun PTFE fabric. A 10 mL syringe was loaded with the desired amount of spinning solution and mounted in a syringe pump and the flow rate was set to 0.2 ml/hr. A stainless steel substrate was loaded on a mandrel which was mounted on a rotating arm and set to rotate at 60 RPM. The collection distance was set to approximately 7 inches. The voltage used to electrospin was between 13-15 kV. An SEM image of the sample, after sintering, is shown in FIG. 5. Average fiber diameters were determined to be 0.837 μm+/−0.117 μm.

Example 4

Figure 6:
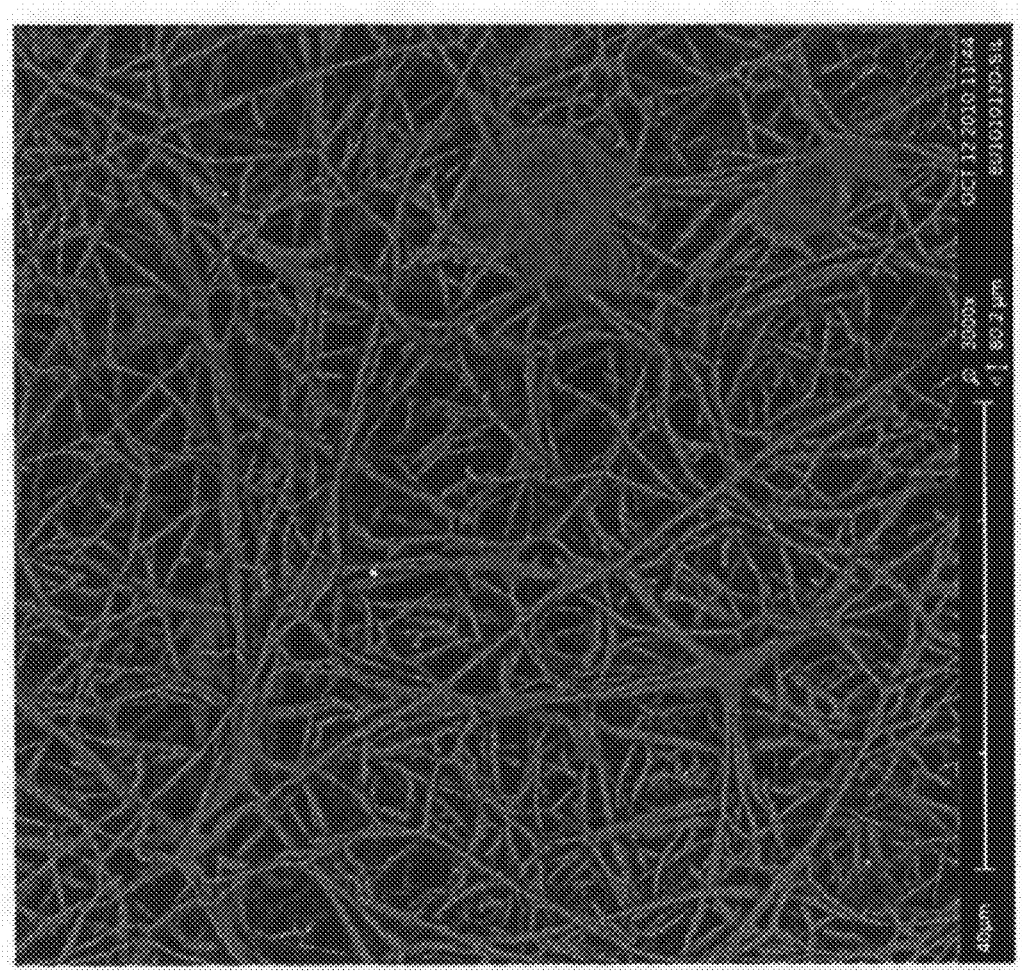
FIG. 6 is a SEM micrograph of PTFE fibers containing approximately 2500 ppm of active silver (Smartsilver® WS), electrospun from the free surface based apparatus.

PTFE electrospun fibers containing 2500 ppm SmartSilver® WS were also produced via free surface electrospinning using a wire or trough method. The solution was loaded into a bath where a cylindrical roller was used as the charging electrode and was coated with the aforementioned solution. The process used was similar to that discussed in Example 2. The collection electrode was a steel wire and the substrate was a stainless steel sheet. The collection distance used was approximately 140-180 cm and the voltage used was 60-80 kV. The sheets were collected using multiple passes of the substrate over the charging electrode. An SEM image of the sample, after sintering, is shown in FIG. 6. Average fiber diameters were determined to be 0.408 μm+/−0.086 μm.

Example 5

Silver nanoparticles (SN) can be produced by reacting silver nitrate ($AgNO_3$) with PEO in solution. These nanoparticles were made by first dissolving PEO (40 g) in deionized water (100 ml) by rolling or stirring at room temperature for 24 hours producing a yellowish, viscous mixture. Silver nitrate was then added to the PEO/water mixture and allowed to react for at least 24 hours and the solution gradually darkened over time. After the reaction was complete the mixture is a dark grey-black, viscous mixture. The PEO/SN/water mixture is then added to 1000 ml of D-210 PTFE dispersion. SNs were loaded such that the final fiber samples contain approximately 1000 ppm of SNs assuming complete conversion of silver nitrate to elemental silver. The final solution was allowed to roll for over 48 hours to produce a viscous, grey-green solution. The resultant viscosity of this mixture was measured at 2.5 RPMs using a #25 spindle at 25° C. taken with a Brookfield LV Viscometer and determined to be approximately 104,000 cP.

Figure 7:
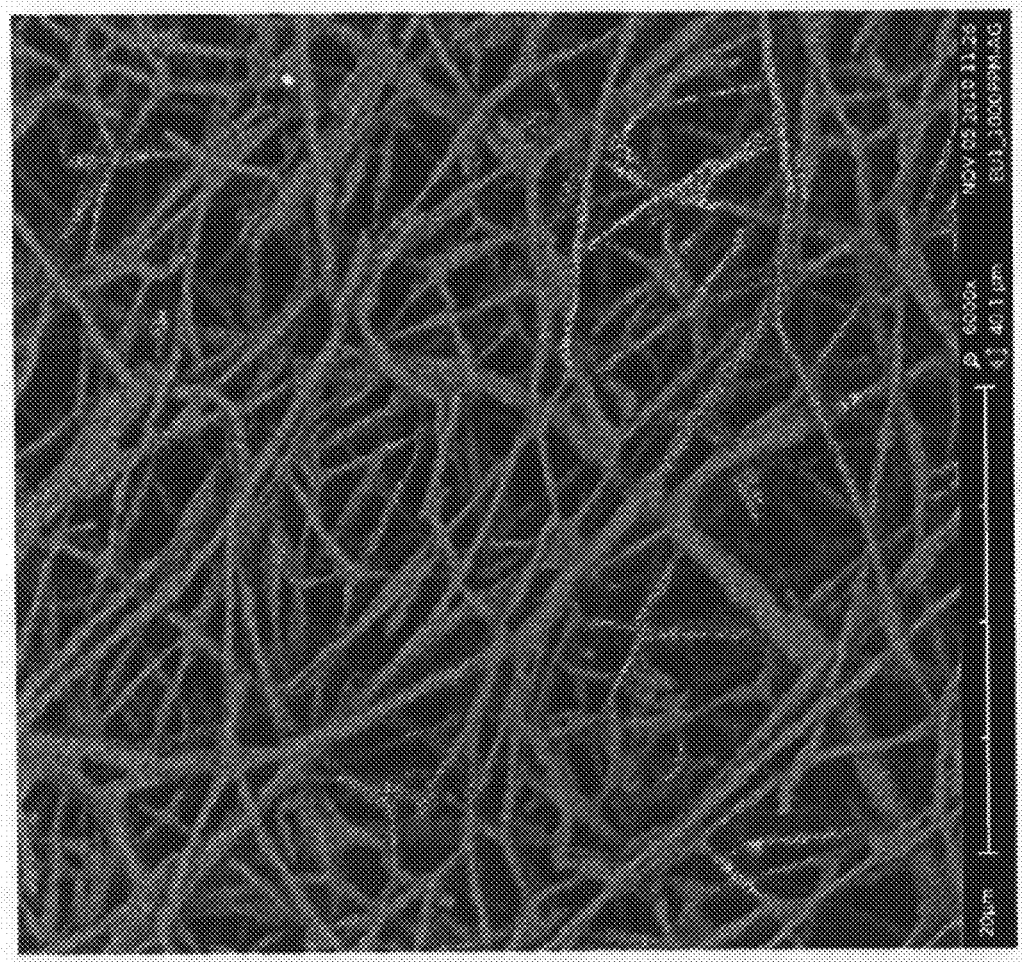
FIG. 7 is a SEM micrograph of PTFE fibers containing approximately 1000 ppm of elemental silver nanoparticles, electrospun from the free surface based apparatus.

PTFE electrospun fibers containing 1000 ppm silver nanoparticles were produced via free surface electrospinning using a wire or trough method. The solution was loaded into a bath where a cylindrical roller was used as the charging electrode and was coated with the aforementioned solution. The process used was similar to that discussed in Example 2. The collection electrode was a steel wire and the substrate was a stainless steel sheet. The collection distance used was approximately 140-180 cm and the voltage used was 60-80 kV. The sheets were collected using multiple passes of the substrate over the charging electrode. An SEM image of the sample, after sintering, is shown in FIG. 7. Average fiber diameters were determined to be 0.384 μm+/−0.059 μm.

Example 6

Titanium dioxide ($TiO_2$) (rutile) from Nanostructured and Amorphous Materials Inc. was dispersed in water (40% solids) with a particle size between 30-50 nm. The $TiO_2$ slurry was added directly to Daikin D-210 PTFE dispersion. $TiO_2$ was loaded such that the final fiber samples contain approximately 4 to 10 wt % of $TiO_2$. The final solution was allowed to roll for over 48 hours to produce a viscous, beige solution. The resultant viscosity of this mixture was measured at 2.5

RPMs using a #25 spindle at 25° C. taken with a Brookfield LV Viscometer to be approximately 83,000 cP (4%) and 67,000 cP (10%).

Figure 8:
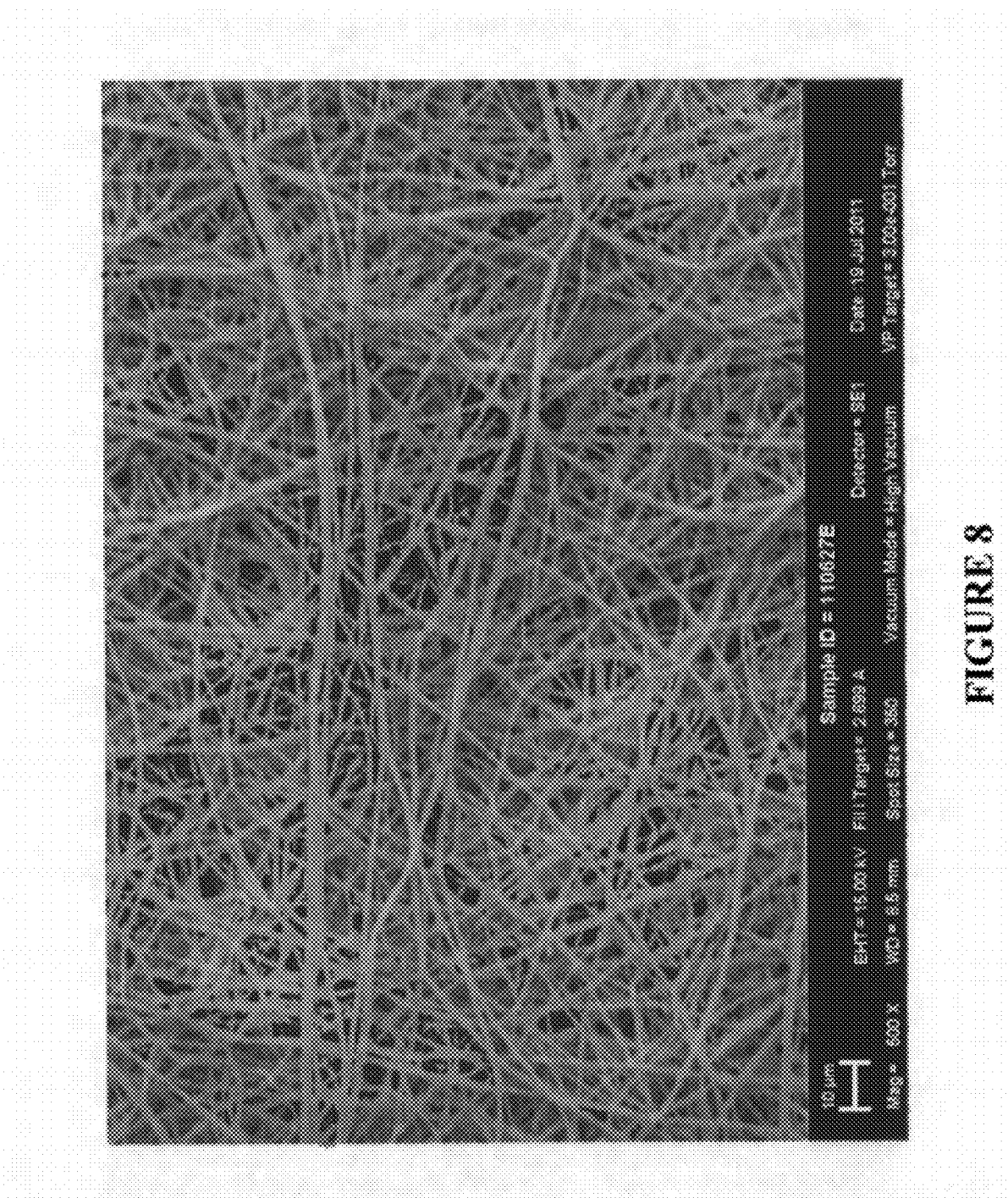
FIG. 8 is a SEM micrograph of PTFE fibers containing approximately 4% titanium dioxide nanoparticles, electrospun from the free surface based apparatus.
Figure 9:
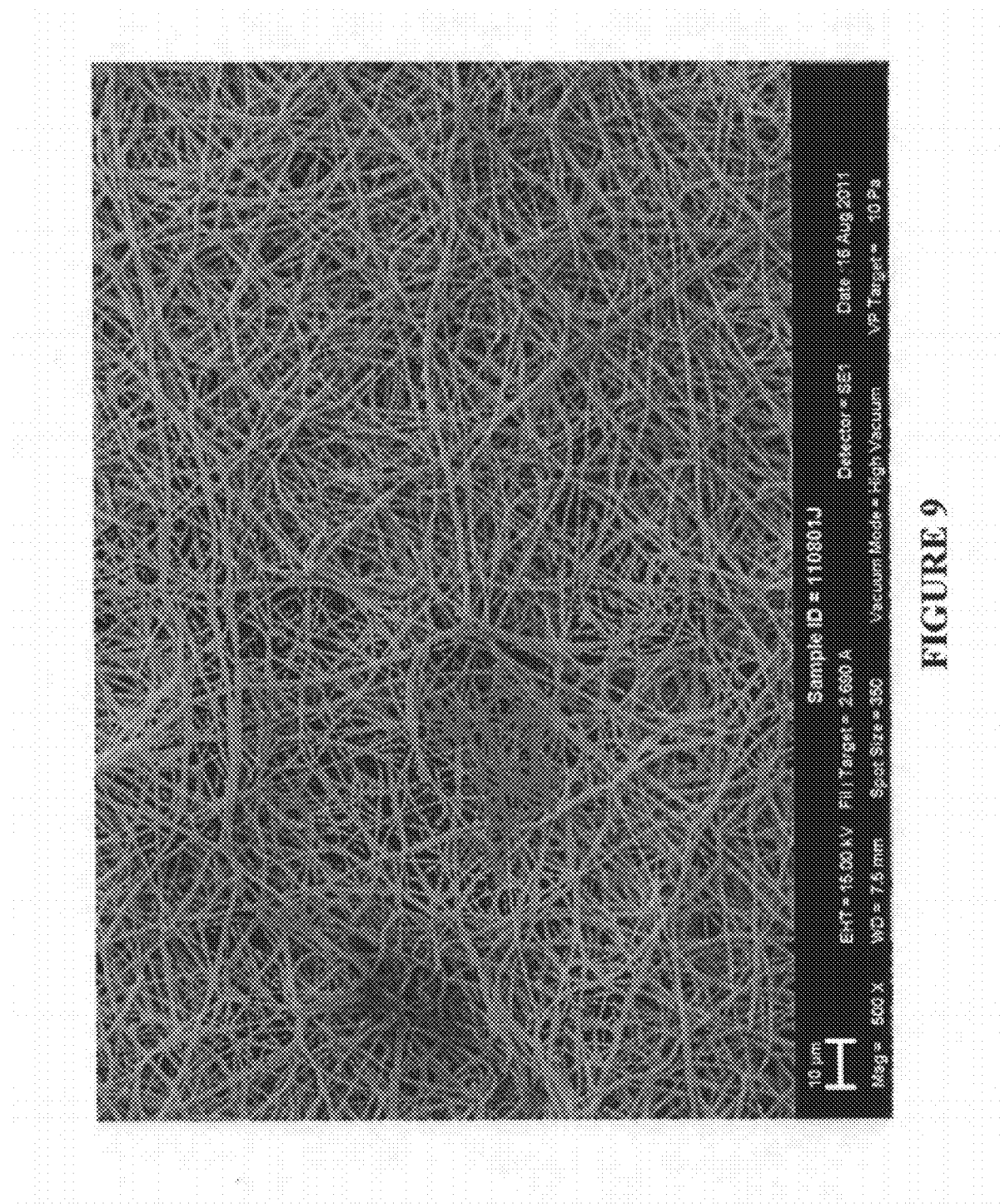
FIG. 9 is a SEM micrograph of PTFE fibers containing approximately 10% titanium dioxide nanoparticles, electrospun from the free surface based apparatus.

PTFE electrospun fiber fabric containing 4 and 10% $TiO_2$ was produced via free surface electrospinning using a wire or trough method. The dispersions were loaded into a bath where a cylindrical roller was used as the charging electrode and was coated with the aforementioned solution. The process used was similar to that discussed in Example 2. The collection electrode was a steel wire and the substrate was a stainless steel sheet. The collection distance used was approximately 140-180 cm and the voltage used was 60-80 kV. The sheets were collected using multiple passes of the substrate over the charging electrode. SEM images of the espun PTFE fabric containing 4 and 10% $TiO_2$, after sintering, are shown in FIGS. 8 and 9 respectively. A summary of characterization techniques performed on the samples are shown in Table 2 for the 4% $TiO_2$ containing sample and in Table 3 for the 10% $TiO_2$ sample.

TABLE 2

| | |
|---|---|
| Avg. Fiber Diameter and Std. Dev. (μm) | 1.02 ± 0.129 |
| Tensile Strength (Pa) | 365 ± 36 |
| Elongation (%) | 195 ± 20 |
| Gurley (sec/100 cc) | 4.7 ± 0.4 |
| Mean Pore Diameter (μm) | 2.27 ± 0.06 |
| Bubble Point Diameter (μm) | 3.264 ± 0.06 |
| Basis Weight (g/m2) | 17.32 ± 0.32 |
| Thickness (μm) | 43.4 |
| Titanium (% by weight) EDAX | 2.07 |

TABLE 3

| | |
|---|---|
| Avg. Fiber Diameter and Std. Dev. (μm) | 0.787 ± 0.093 |
| Tensile Strength (Pa) | 310 ± 33 |
| Elongation (%) | 134 ± 17 |
| Gurley (sec/100 cc) | 6.7 ± 0.7 |
| Mean Pore Diameter (μm) | 2.09 ± 0.22 |
| Bubble Point Diameter (μm) | 2.72 ± 0.05 |
| Basis Weight (g/m2) | 24.97 ± 0.97 |
| Thickness (μm) | 48.3 |
| Titanium (% by weight) EDAX | 4.63 |

Example 7

These doped PTFE non-woven materials were tested for their antimicrobial efficacy using AATCC 100-2004 Assessment of Antimicrobial Finishes on Textile Material method. Swatches treated and untreated fabric were cut in diameter of 4.8±1 cm disc and were inoculated with 1 ml of test organism in a concentration of 1–2×105 cfu/ml. Each stack was aseptically transferred to sterile screw cap jars and incubated at 350±2 C. Treated and untreated samples with no inoculums were also set up as control. After zero hour and time specified by sponsor of study, sets of treated and untreated swatches were removed from incubator and were neutralized with 100 ml neutralizer. Plate counts were performed and incubation was carried out according to each organism's requirement per AATCC 100 standard. The test organism in each case was *Escherichia Coli* (*E. Coli*). Results are shown in Table 4.

TABLE 4

Antimicrobial properties of various PTFE materials.

| Sample | Zero Contact Time | 24-hour Contact Time | % reduction |
|---|---|---|---|
| 2,500 ppm Smartsilver WS (Example 4) | $7.2 \times 10^5$ | $1.10 \times 10^3$ | 99.8% |
| 1,000 ppm SN (Example 5) | $3.5 \times 10^5$ | 0 | >99.99% |
| 1,000 ppm Smartsilver WS | $8.5 \times 10^5$ | $1.17 \times 10^5$ | 86% |
| 250 ppm Smartsilver WS | $3.5 \times 10^5$ | $3.3 \times 10^7$ | <0% |
| Control (PTFE with no silver) | $2.5 \times 10^5$ | $3.5 \times 10^6$ | <0% |
| Control | $2.4 \times 10^5$ | $8.5 \times 10^7$ | <0% |

The results from the antimicrobial testing indicate that a loading of at least 250 ppm of Smartsilver® WS was necessary to show any reduction of *E. Coli* after a 24-hour exposure period. Additionally, with increased loadings of Smartsilver® WS more bacteria were killed in the observed time period. The silver nanoparticle (SN) loaded PTFE proved to be more effective than the Smartsilver® WS and killed >99.99% of the *E. Coli* bacteria after a 24-hour period.

The invention claimed is:

1. A method of making a nonwoven mat comprising one or more antimicrobial agents, comprising:
   providing a dispersion comprising:
      a fluorinated polymer;
      a fiberizing polymer;
      one or more antimicrobial agents; and
      a solvent;
   electrospinning said dispersion to give a mat precursor; and
   heating said mat precursor at a temperature and for a time sufficient to remove said solvent and said fiberizing polymer, in order to form a nonwoven mat.

2. The method of claim 1, wherein said electrospinning comprises:
   providing an apparatus comprising a charge source and a target a distance from said charge source;
   providing a voltage source to create a first charge at said charge source and an opposing charge at said target wherein said dispersion is electrostatically charged by contact with said charge source; and
   collecting said electrostatically charged dispersion on said target.

3. The method of claim 1, wherein the one or more antimicrobial agents are selected from the group consisting of silver, silver compounds, metal oxides, metal sulfides, and mixtures thereof.

4. The method of claim 3, wherein the one or more antimicrobial agents comprise silver nanoparticles.

5. The method of claim 3, wherein the metal oxides and metal sulfides are selected from the group consisting of titanium dioxide, selenium sulfide, cadmium oxide, zinc oxide, and mixtures thereof.

6. The method of claim 1, wherein said nonwoven mat comprises the one or more antimicrobial agents in an amount of between about 10 ppm and about 10,000 ppm.

7. The method of claim 6, wherein said nonwoven mat comprises the one or more antimicrobial agents in an amount of between about 1,000 ppm and about 5,000 ppm.

8. The method of claim 1, wherein said fluorinated polymer is provided in the form of a resin comprising about 50% to about 80% polymer solids by weight.

9. The method of claim 1, wherein said fluorinated polymer has an average particle size of between about 0.1 μm and about 0.3 μm.

10. The method of claim 1, wherein said fluorinated polymer comprises polytetrafluoroethylene.

11. The method of claim 1, wherein said fluorinated polymer is selected from the group consisting of fluorinated ethylene propylene (FEP), polyvinylidene fluoride (PVDF), perfluoroalkoxy (PFA), a copolymer of tetrafluoroethylene, hexafluoropropylene and vinylidene fluoride (THV), poly(ethylene-co-tetrafluoroethylene) (ETFE), ethylene chlorotrifluoroethylene (ECTFE), PCTFE (polychlorotrifluoroethylene), and copolymers, blends, and derivatives thereof.

12. The method of claim 1, wherein the amount of fiberizing polymer is between about 3.0 and about 5.5 percent by weight of the amount of fluorinated polymer.

13. The method of claim 1, wherein said fiberizing polymer has a solubility in said solvent of greater than about 0.5 weight percent at room temperature.

14. The method of claim 1, wherein said fiberizing polymer is polyethylene oxide.

15. The method of claim 14, wherein the polyethylene oxide has a number average molecular weight of from about 50,000 amu to about 4,000,000 amu.

16. The method of claim 1, wherein said solvent is water.

17. The method of claim 1, wherein said dispersion has a viscosity of greater than 50,000 cP.

18. The method of claim 17, wherein the viscosity is from about 70,000 cP to about 150,000 cP.

19. The method of claim 1, wherein the voltage used during electrospinning is about 2,000 to about 100,000 volts.

20. The method of claim 1, wherein the heating is conducted between about 350° C. and about 485° C.

21. A method of making a nonwoven polytetrafluoroethylene mat comprising one or more antimicrobial agents, comprising:
  providing a dispersion comprising:
    polytetrafluoroethylene;
    polyethylene oxide;
    one or more antimicrobial agents selected from the group consisting of silver, silver compounds, metal oxides, metal sulfides, and mixtures thereof; and
    a solvent;
  electrospinning said dispersion to give a polytetrafluoroethylene mat precursor; and
  heating said polytetrafluoroethylene mat precursor at a temperature and for a time sufficient to remove said solvent and polyethylene oxide, in order to form a nonwoven polytetrafluoroethylene mat.

* * * * *